US007488582B2

(12) United States Patent
Pourquie et al.

(10) Patent No.: US 7,488,582 B2
(45) Date of Patent: Feb. 10, 2009

(54) NUCLEIC ACIDS AND ASSOCIATED DIAGNOSTICS

(75) Inventors: Olivier Pourquie, Kansas City, MO (US); Karen Staehling-Hampton, Kansas City, MO (US); Kym Delventhal, Kansas City, MO (US)

(73) Assignee: Stowers Institute For Medical Research, Kansas City, MO (US)

( * ) Notice: Subject to any disclaimer, the term of this patent is extended or adjusted under 35 U.S.C. 154(b) by 0 days.

(21) Appl. No.: 11/555,982

(22) Filed: Nov. 2, 2006

(65) Prior Publication Data

US 2007/0166732 A1    Jul. 19, 2007

Related U.S. Application Data

(60) Provisional application No. 60/732,887, filed on Nov. 2, 2005.

(51) Int. Cl.
*C12Q 1/68* (2006.01)
*C12P 19/34* (2006.01)
*C07H 21/04* (2006.01)

(52) U.S. Cl. .......................... 435/6; 435/91.2; 536/24.33
(58) Field of Classification Search ..................... 435/6, 435/91.2; 536/24.33
See application file for complete search history.

(56) References Cited

FOREIGN PATENT DOCUMENTS

WO    WO 02/068579 A2 *    9/2002

OTHER PUBLICATIONS

Whittock et al. mutated MESP2 causes spondylocostal dysostosis in humans. Am J Hum Genet., vol. 74, pp. 1249-1254, Jun. 2004.*
Turnpenny et al. Novel mutations in DLL3, a somitogenesis gene encoding a ligand for the notch signalling pathway, cause a consistent pattern of abnormal vertebral segmentation in spondylocostal dysostosis. J Med Genet, vol. 40, pp. 333-339, 2003.*
Maisenbacher, M.K., Han, J. O'Brien, M.L., Tracy, M.R., Erol, B., Schaffer, A.A., Dormans, J.P., Zackai, E.H. and Kusumi, K. Molecular analysis of congenital scollosis: a candidate gene approach; Human Genetics; 2005; 416-419, vol. 116.
Weinmaster, G. and Kintner, C.; Modulation of Notch Signaling During Somitogenesis; Annual Review of Cell and Development Biology; 2003; 367-395; vol. 19.
Bonafe, L., Giunta, C., Gassner, M., Steinmann, B. and Superti-Furga, A.; A cluster of autosomal recessive spondylocostal dysostosis caused by three newly identified DLL3 mutations segregating in a small village; 2003; 28-35; vol. 64.
Mortier, G.R., Lachman, R.S., Bocian, M, and Rimoin, D.L.; Multiple Vertebral Segmentation Defects: Analysis of 26 New Patients and Review of the Literature; American Journal of Medical Genetics 1996; 310-319; vol. 61.
Pourquie, O.; Vertebrate Somitogenesis; Annual Review of Cell and Development Biology; 2001; 311-350; vol. 17.

Sparrow, D.B., Clements, M., Withington, S.L., Scott, A.N., Novotny, J., Sillence, D., Kusimi, K., Beddington, R.S.P. and Dunwoodie, S.L.; Diverse requirements for Notch signalling in mammals; The International Journal of Developmental Biology; 2002; 365-374; vol. 46.
Whittock, N.V., Ellard, S., Duncan, J., de Die- Smulders, Cem, Vles, J.S.H. and Turnpenny, P.D.; Pseudodominant inheritance of spondylocostal dysostosis type 1 caused by two familial delta-like 3 mutations; Clnical Genetics; 2004; 67-72; vol. 66.
Turnpenny, P.D. and Kusumi, K.; DLL3 and Spondylocostal Dysostosis In; Inborn Errors of Development Oxford University Press, New York; 2003; 470-481.
Sparrow, D.B., Chapman, G., Wouters, M.A., Whittock, N.V., Ellard, S., Fatkin, D., Turnpenny, P.D., Kusumi, K., Sillence, D. and Dunwoodie, S.L.; Mutation of the Lunatic Fringe Gene in Humans Causes Spondylocostal Dysostosis with a Severe Vertebral Phenotype; The American Journal of Human Genetics; 2006; 28-37; vol. 78.
Turnpenny, P.D., Whittock, N., Duncan, J., Dunwoodie, S., Kusumi, K., Ellard, S.; Novel mutations in DLL3, a somitogenesis gene encoding a ligand for the Notch signalling pathway, cause a consistent pattern of abnormal vertebral segmentation in spondylocostal dysostosis; J. Med Genet; 2003; 333-339; vol. 40.
Pourquie, O., Kusumi, K.; When body segmentation goes wrong; Clin Genet; 2001; 409-416; vol. 60.
Whittock, N.V.; Sparrow, D.B.; Wouters, M.A., Sillence, D., Ellard, S., Dunwoodie, S.L., and Turnpenny, P.D.; Mutated MESP2 Causes Spondylocostal Dysostosis in Humans; The American Journal of Human Genetics; 2004; 1249-1254; vol. 74.
Bulman, M.P., Kusumi, K., Frayling, T.J., McKeown, C., Garrett, C., Lander, E.S., Krumlauf, R., Hattersley, A.T., Ellard S. and Turnpenny, P.D.; Mutations in the human Delta homologue. DLL3, cause axial skeletal defects in spondylocostal dysostosis; Nature Genetics; 2000; 438-441; vol. 24.
Saga, Y., Hata, N., Koseki, H. and Taketo, M.M.; Mesp2: a novel mouse gene expressed in the presegmented mesoderm and essential for segmentation initiation: Genes & Development; 1997; 1827-1839; vol. 11.
Romeo, M.G., Distefano, G., Di Bella, D., Mangiagli, A., Caltabiano, L., Roccaro. S. and Mollica, F.; Familial Jarcho-Levin syndrome; Clinical Genetics; 1991; 253-259, vol. 39.
Campbell, R.M. and Smith, J.T.; Response to "Spondylothoracic Dysplasia Syndrome: A Series of 27 New Cases" by Cornier et al.; American Journal of Medical Genetics; 2004; p. 132 vol. 128A.

(Continued)

*Primary Examiner*—Suryaprabha Chunduru
(74) *Attorney, Agent, or Firm*—Bryan Cave LLP

(57) ABSTRACT

The present invention relates to methods of diagnosing spondylocostal dysostosis (SCD) disorders, such as Jarcho-Levin syndrome, in humans for use in genetic counseling and linkage analyses. Methods and compositions for measuring the presence or absence of a specific mutation to Mesp2 associated with Jarcho-Levin syndrome, alone or in combination with other mutations associated with spondylocostal dysostosis, are provided.

11 Claims, 3 Drawing Sheets

OTHER PUBLICATIONS

Dale, J.K., Maroto, M., Dequeant, M.L., Malapert, P., McGrew, M., Pourquie, O., Periodic motch inhibition by lunatic fringe underlies the chick segmentation clock: Nature; 2003, vol. 421.

Pourquie, Olivier; The Segmentation Clock: Converting Embryonic Time into Spatial Pattern; Science Magazine; 2003; 328-330 vol. 301.

Cornier, A.S., Ramirez, N., Arroyo, S., Acevedo, J., Garcia, L., Carlo, S. and Korf, B.; Phenotype Characterization and Natural History of Spondylothoracic Dysplasia Syndrome: A Series of 27 New Cases; American Journal of Medical Genetics ; 2004; 120-126 vol. 128A.

M.N. Kuppuswamy et al., "Single nucleotide primer extension to detect genetic diseases: Experimental application to hemophilia B (factor IX) and cystic fibrosis genes," Proc. Natl. Acad. Sci. USA, pp. 1143-1147 (1991).

N.V. Whittock et al., "Mutated MESP2 Causes Spondylocostal Dysostosis in Humans," Am. J. Hum. Genet., No. 74, pp. 1249-1254 (2004).

* cited by examiner

NUCLEIC ACIDS AND ASSOCIATED DIAGNOSTICS

This application claims benefit to U.S. Provisional Patent Application Ser. No. 60/732,887, filed Nov. 2, 2005.

FIELD OF THE INVENTION

The invention relates to methods and compositions for the detection and diagnosis of spondylocostal dysostoses disorders. In particular, the invention relates to a methods, kits, and compositions for detecting carriers of spondylocostal dysostoses, in particular Jarcho-Levin syndrome, for use in genetic counseling.

BACKGROUND OF INVENTION

I. Segmentation

Segmentation is a basic characteristic of many animal species ranging from invertebrates, such as insects, to vertebrates, such as humans. Body segmentation usually corresponds to repetition of similar structures consisting of derivatives from the three embryonic germ layers. In humans, segmentation is most obvious at the level of the vertebral column and its associated musculature, as well as in the peripheral nervous system. The segmented distribution of the vertebrae derives from the earlier metameric pattern of the embryonic somites.

Segmentation is visualized morphologically by the sequential formation of bilateral blocks of cells, the somites, from the rostral extremity of the presomitic mesoderm (PSM). In most vertebrates, somites are further subdivided into an anterior and posterior compartment. This subdivision is important for later patterning events, such as the formation of the vertebrae which are formed through the fusion of the posterior part of a somite to the anterior part of the consecutive somite in a process called resegmentation. This partitioning of the somite is also critical for establishing the peripheral nervous system (PNS) segmentation since motor neuron axons and neural crest cells are only allowed to migrate in the anterior part of the somite, thus resulting in the segmented aspect of the PNS. Formation of the somites occurs in the rostral PSM and relies on a molecular oscillator called the segmentation clock which requires both Notch and Wnt signaling. (Pourquie, *Annual Review Cell Dev Biol*, 17-311-350 (2001).)

II. Genetically Defective Segmentation

In humans, defects in the early stages of the vertebral column formation can result in a wide range of vertebral and rib malformations often grouped as congenital scoliosis or spondylocostal dysostoses (SCD). These malformations are very severe but the frequency of such malformations is quite low (1 or 2 per 10,000 births). The vertebral anomalies result in worsening spinal deformity with growth. Surgical spine fusion may be necessary to correct and stop the spinal curvature. These disorders are characterized radiologically by multiple vertebral segmentation defects and rib anomalies, which are frequently misaligned with their points of fusion and sometimes reduced in number. (Turnpenny et al, J. Med. Genet 40:333-339 (2003).)

Sporadic cases of SCD occur more commonly than familial ones and are more likely to be associated with multiple congenital abnormalities. In contrast, monogenic forms more commonly demonstrate autosomal recessive (AR) rather than autosomal dominant (AD) inheritance. Associated features in familial cases include anal and urogenital anomalies, congenital heart disease, limb abnormalities, plagiocephaly-torticollis sequences, and inguinal herniae in males.

Thus far, only three genes, Delta-like3 (DLL3), Lunatic fringe (Lfng) and Mesoderm postertior 2 (Mesp2), each of which is linked to the segmentation clock oscillator, have been associated with such heritable syndromes in humans. Twenty four distinct mutations have been found in DLL3 (SCD1 [MIM 277300]) and associated with SCD. (Bulman et al. 2000; Sparrow et al. 2002; Bonafé et al. 2003; Turnpenny et al. 2003; Whittock et al, 2004a). A single, missense mutation was identified in Lfng in a highly conserved phenylalanine close to the active site of the enzyme that caused it to become inactive. Sparrow, et at (2006). A single mutation to Mesp2 (SCD)2 [MIM 608681]) has also been identified (Whittock et al. 2004b).

In the mouse, additional and different mutations to the Notch signaling pathway, which is central to somite formation, have been identified (e.g. Notch1, DLL3, DLL1, Lfng, Psen1, and Csl), and mutation to a downstream target gene (hes7) also results in abnormal somitogenesis. Reviewed by Weinmaster and Kintner (2003).

The aforementioned studies recognized that the molecular defects underlying most of the congenital scoliosis cases remain unknown. In fact, most cases of congenital scoliosis are not identified in humans until a fetus is well-developed, or a child is born. Presently, because the underlying cause of most of these disorders is unknown, the ability to proactively identify families and couples at risk for having children with any of these disorders is severely limited or impossible.

SUMMARY OF THE INVENTION

The current invention provides methods, kits, and compositions for diagnosing and predicting the likelihood of spondylocostal dysostosis/Jarcho-Levin syndrome or spondylothoracic dysplasia. To date, such diagnostic methods and compositions have been unavailable. These methods and compositions will be potentially useful for providing genetic counseling to affected families and those at risk for carrying genetic mutations associated with these disorders. These methods and compositions also provide early diagnostic tools to determine if a newborn or young adolescent is afflicted with SCD, and if so, whether a mild or severe form of SCD is likely to develop, Early diagnosis is key to providing early treatment to ameliorate the affects of these conditions.

In sequencing a subset of genes associated with the oscillator function, a novel mutation in the Mesp2 gene (schematically shown in FIG. 1 and referred to herein as "E103stop") was identified. This mutation was identified in humans as causing a very severe vertebral column syndrome commonly called Jarcho-Levin syndrome. This syndrome is often found in individuals of Puerto-Rican descent. Here, the mutation was initially isolated from a subject of Puerto-Rican descent suffering from Jarcho-Levin syndrome. The presence of the mutation was subsequently confirmed in other patients of Puerto-Rican descent suffering from Jarcho-Levin syndrome (e.g. Example 1, Table 1).

A simple test to screen for the E103stop mutation has been devised, and as demonstrated by the results herein, this test may have a highly predictive value for these patients. Additionally, identification of the genes underlying these vertebral defects, such as Jarcho-Levin syndrome, will find important applications in the genetic counseling of affected families, as well as, for those at risk of carrying a mutation (i.e. heterozygotes) but lacking any phenotypic indications of it.

As such, the invention provides a method for screening a subject to determine whether the subject is either a carrier or is afflicted with spondylocostal dysostosis or with spondylothoracic dysplasia. The method detects the presence or absence of a mutation to the Mesp2 nucleic acid in a biological sample from the subject, whereby detection of a mutant Mesp2 nucleic acid indicates a genetic mutation giving rise to spondylocostal dysostosis. An appropriate biological sample, such as bodily fluid, tissue, or epithelial cells, will include genomic DNA of the subject. In certain cases where the subject is human and homozygous for the E103stop mutation to Mesp2, the genetic mutation gives rise to Jarcho-Levin syndrome.

The invention further provides a method for detecting the presence or absence of a Spe I restriction enzyme site in exon 1 of the Mesp2 gene. Presence of the Spe I restriction site is indicative of the mutation giving rise to Jarcho-Levin syndrome. This indication is further supported when digestion with Spe I results in nucleic acid fragments of a predicted size(s). The skilled artisan will recognize that the predicted size(s) of the fragments produced will be dependent upon both digestion with Spe I, the length of the starting material, and the presence or absence of other restriction enzymes. In all cases, the size(s) of the fragments can be predicted without undue experimentation using the teachings provided herein.

The present invention can be used for diagnosing a subject with Jarcho-Levin syndrome. Further, the invention can be used for diagnosing a subject as a carrier of (i.e. heterozygous for) a mutation that in its homozygous form yields Jarcho-Levin syndrome. The method can include obtaining genomic DNA from a subject, sequencing the genomic DNA, and analyzing the genomic sequence for the presence of absence of the mutation, as represented by SEQ ID NO. 2, a fragment or complement thereof, in an Mesp2 gene. Alternatively, the method can be used to hybridize a nucleic acid probe comprising SEQ ID NO. 2, or a portion thereof, to a biological sample from a subject who is a carrier of the E103stop mutation. A preferred method of using the invention comprises single base pair primer extension. Appropriate primers anneal adjacent to the E103stop position in Mesp2 and extend either in the presence or in the absence of the mutation.

Kits for screening a subject to determine whether the subject is a carrier of, or is afflicted with spondylocostal dysostosis, such as Jarcho-Levin syndrome, or with spondylothoracic dysplasia are also provided by the invention. The kit includes a means for detecting the presence or absence of Mesp2 nucleic acids in a biological sample from a subject such as a human. In particular, detection in the genomic DNA from the biological sample of the substitution of a thymine for a guanine at nucleotide position 307 of exon 1 of Mesp2 (i.e. an E103stop mutation) indicates a genetic mutation linked to spondylocostal dysostosis or spondylothoracic dysplasia. In certain subjects, the genetic mutation gives rise to Jarcho-Levin syndrome. A kit can also be used for detecting the presence or absence of a Spe I restriction enzyme site in exon 1 of the Mesp2 gene that is associated with the E103stop mutation.

Kits may also be used to detect the presence or absence of SEQ ID NO. 2, or a fragment thereof, that includes the E103stop mutation. For example, a nucleic acid probe may comprise the entire SEQ ID NO. 2, or the probe may comprise two fragments of SEQ ID NO. 2 that when ligated to each other include the E103stop mutation. It is recognized that such nucleic acid probes comprise at least 8 contiguous bases of SEQ ID NO. 2, more preferably at least 9, at least 10, at least 11, at least 12, at least 13, at least 14, at least 15, at least 16, at least 17, at least 18, at least 19, or even at least 20 or more contiguous bases of SEQ ID NO. 2 either initially as a single fragment or forming a single fragment after ligation.

A preferred kit will include a primer suitable for single base pair primer extension or single nucleotide polymorphism (SNP) detection. Detection may comprise restriction fragment length polymorphism (RFLP) analysis and/or may be used in conjunction with software to size and genotype the data. An advantage of single base pair primer extension is that homozygosity and heterozygosity for a mutation or multiple mutations may be ascertained. Thus, kits of this nature may be useful for diagnosing whether an individual, e.g. a newborn, infant, or adolescent, is afflicted with SCD, in particular Jarcho-Levin syndrome, prior to the appearance of diagnostic, phenotypic symptoms or is a carrier, regardless of age, showing no phenotypic symptoms.

Methods and kits for the screening of a subject and/or his or her family for Jarcho-Levin syndrome are presented. Such methods and kits may be useful in the genetic counseling of such individuals and families. Such kits may be used in combination with restriction enzymes. For example, the restriction enzyme Spe I may be included in the kit with instructions indicating the expected sizes of DNA fragments that are diagnostic for the presence, or absence, of Jarcho-Levin syndrome or other forms of SCD under various digest conditions. One of skill in the art will recognize that the expected sizes of DNA fragments depends upon the starting materials, combination of restriction enzymes, and desired purposes.

The invention further provides a nucleic acid probe that includes SEQ ID NO. 2, or a fragment thereof, and is useful in the detection of a mutation in Mesp2 giving rise to Jarcho-Levin syndrome or spondylocostal dysostosis. Alternatively, the probe comprises at least about 50%, about 65%, about 75%, about 85%, about 95%, about 96%, about 97%, about 98%, or about 99% or higher homology to SEQ ID NO. 2, a fragment or complement thereof.

The probe may be labeled with a detectable marker such as enzymes, biotin, radionuclides, fluorophores, chromophores, luminophores, enzyme inhibitors, coenzymes, luciferins, paramagnetic metals, spin labels, chemiluminescent agents, radioisotopes, enzyme substrates, electron dense reagents, magnetic particles, electrochemically active moieties, mass labels, or similar compositions.

Methods and kits can also be used for screening inherited disease(s), with the steps including contacting a biological sample from a subject that includes the subject's genomic DNA with a probe comprising an oligonucleotide capable of specifically hybridizing with a disease-associated polynucleotide sequence and detecting the presence or absence of the disease-associated sequence in the patient's nucleic acids. Preferably, the nucleic acid probe is SEQ ID NO. 2, or a fragment or complement thereof.

The kits and methods can be used for detecting the E103stop mutation alone or in combination with other mutations associated with SCD such as the 500-503 dup mutation [MIM 605195.0001] to Mesp2, mutation to DLL3, mutation to Lfng, or mutation to Jag1. Such combinations are expected to be useful in rapid screening for SCDs. It is likely that any positive results for a SCD would be rescreened, or a second sample from a subject would be screened, to confirm such results prior to a final diagnosis.

The methods and kits of the invention can include the step of polymerase chain reaction (PCR) amplification and/or restriction enzyme digestion, for example with Spe I. Furthermore, the methods and kits of the invention can include determination of the SEQ ID NO. 2 nucleotide sequence, its complimentary sequence, or a fragment thereof by selecting a method from the group consisting of PCR-RFLP, ligase chain reaction (LCR), oligotyping using sequence specific primers, oligotyping using sequence specific oligonucleotide probes, single-stranded conformation polymorphism, direct sequencing, single base pair primer extension, or other similar method known in the art. A preferred method and kit will include single base pair primer extension.

DETAILED DESCRIPTION

Figure 1:
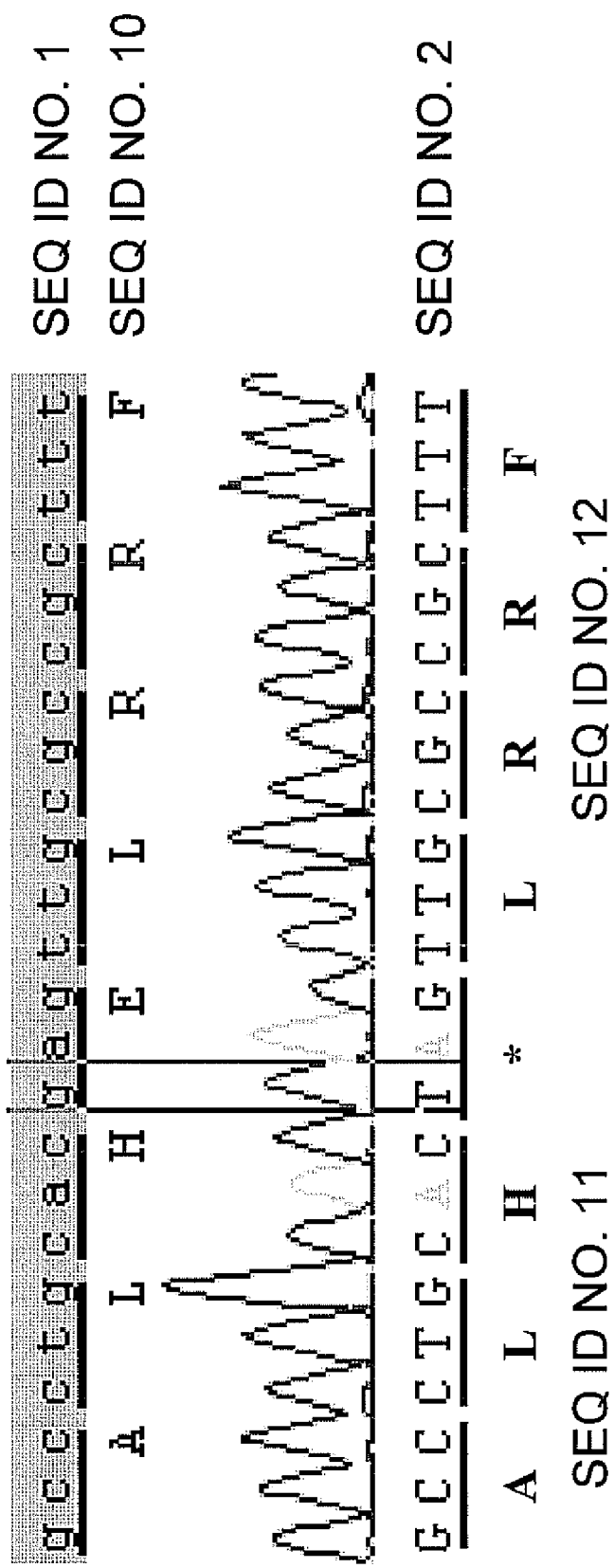
FIG. 1. Detection of the E103stop mutation by DNA sequencing. The DNA sequence (GCCCTGCACGAGTTGCGCCGC, SEQ ID NO. 1) and amino acid sequence (ALHELRRF, SEQ ID NO, 10) of Mesp2 from Genbank were compared with the DNA sequence (GCCCTGCACTAGTTGCGCCGC, SEQ ID NO.2) and translated amino acid sequence (ALH, SEQ ID NO. 11 and LRRF, SEQ ID NO. 12) from a patient diagnosed with Jarcho-Levin syndrome. The mutation yielded a single base pair substitution (307G>T), "E103stop", that is highlighted by a box drawn around it. As shown, the E103stop mutation results in a stop codon.

The present invention relates to methods, kits, and compositions useful for the early diagnosis and screening of subjects for the presence or absence of a mutation to the Mesp2 gene that is linked to a form of spondylocostal dysostosis, or spondylothoracic dysplasia, frequently referred to as Jarcho-Levin syndrome.

I. Human Vertebral Segmentation Defects

Numerous congenital defects of the spinal column have been identified that result from segmentation disruption that include: Kippel-Feil syndrome, spondylocostal dysostosis, Jarcho-Levin syndrome, congenital scoliosis and kyphosis, spondylothoracic dysplasia, Golden-har syndrome, VATER (vertebral-anal-cardiac-tracheo-esophageal-renal) and VATERL (vertebral-anal-cardiac-tracheo-esophageal-renal-limb) associations. Diagnostic classification between these disorders frequently overlaps; although they may be distinguished by the number of vertebrae affected and the severity of the defects. It is likely that the developmental mechanisms that produce these defects involve a common process of somitogenesis.

There is evidence that the Notch pathway controls vertebral segmentation in some animals and humans. This pathway is required for normal somite formation during embryonic development. Vertebrae are derived from somites and therefore mutations in genes associated with the Notch signaling pathway are implicated in the genesis of abnormal vertebral segmentation (AVS). Primary components of the human pathway include four Notch cell-surface receptors that can be activated by three ligands of the Delta class and two of the Jagged (Serrate) class. These interactions are modulated by three Fringe genes.

The affinity of Notch for these components can be modified by differential glysosylation mediated by the fringe protein, encoded by the glycosyl transferase lunatic fringe. This cycling gene is expressed as a wave that sweeps rostrally across the presomitic mesoderm starting from the caudal end. This wave of expression occurs in early development with precise periodicity for each cycle culminating in the segmentation of a somite from the presomitic mesoderm. Lunatic fringe is thus considered a molecular read out of a segmentation clock.

The Notch signaling pathway is intrinsic to the oscillations of the segmentation clock. Disruption of Notch signaling leads to perturbation of the clock and aberrant somite formation. This aberrant formation is the result of disruption of the segmentation clock since expression of cyclical genes (e.g. lunatic fringe, hes1, and hes5) is abnormal. However, it is not yet clear how Notch signaling leads to somite boundary formation.

Forms of AVS showing clear Mendelian inheritance are relatively rare, and the cause of most of these syndromic conditions and associations is unknown. Abnormal vertebral segmentation is most frequently seen in sporadic cases with diverse radiological phenotypes. Mutations in four genes of the Notch signaling pathway have been identified with defects of vertebral patterning: Delta-like 3 (DLL3) in spondylocostal dysostosis/Jarcho-Levin syndrome (Bulman et al., *Nat Genet*, 24: 438-441 (2000)), Mesp2 in spondylocostal dysotosis (Whittock et al., Am J Hum Genet. 74(6): 1249-54 (2004)), and *Lunatic Fringe* (Lfng) (Sparrow DB, Am J Hum Genet 78(1): 28-37 (2006)).

II. Spondylocostal Dysostosis/Jarcho-Levin Syndrome; DLL3 and Lfng

The spondylocostal dysostoses (SCD) are a heterogeneous group of disorders with severe abnormal vertebral segmentation, characterized radiologically by multiple vertebral segmentation defects and rib anomalies. SCD patients exhibit generalized vertebral malformations, rib fusions and a congentical, non-progressive kypho-scoliosis. Genetically, SCD is heterogeneous, with both autosomal-dominant and autosomal-recessive modes of inheritance observed in pedigrees. (Mortier et al., *Am Med Genet*, 61: 310-319 (1996). These diverse SCD phenotypes can either be sporadic or familial. Monogenic SCD families have been reported with both autosomal dominant (AD) and autosomal recessive (AR) inheritance. Associated features in familial SCD include anal and urogenital anomalies, congenital heart disease, limb abnormalities, plagiocephaly-torticollis sequence, and inguinal herniae in males.

Mutations in the DLL3 gene, which encodes a ligand for the Notch receptor, cause at least one form of the disorder. Turnpenny et al. 2006 identified several of these mutations to DLL3, and they include the following base changes: 318 G>C of exon 3; 425 T>A of exon 5; 515 T>G of exon 5; 546 C>G of exon 5; 653 T>C of exon 6; 1029 T>C of exon 7; 1356 C>T of exon 8; 1547 G>T of exon 8; 1585 C>T of exon 8; 1623 G>A of exon 8; and 1362 G>T of exon 8. (Genbank accession number NM_016941 is the reference source for the mutation positions starting from the translation start position.) Each of these mutations results in an amino acid change. Some cases of SCD have no mutations in DLL3, and, in some of these, linkage to the DLL3 locus at 19q13.1 can be excluded. Within this group, the radiologic phenotype differs mildly from that of DLL3 mutation-positive cases of spondylocostal dysostosis and is variable, suggesting further heterogeneity.

Mutation to the Lfng gene is also linked to at least one form of SCD. LFNG enhances Notch1's ability to be activated by DLL1 and reduces Notch1 signaling when Jagged1 is the activating ligand. Sparrow et al. 2006 identified a mutation to LFNG that resulted in LFNG not being localized to the correct compartment of the cell and being unable to modify Notch signaling in vitro. Sparrow et at, 2006 hypothesized that this mutation, which created a novel MseI restriction enzyme site, resulted in at least one form of SCD. Specifically, the mutation was a missense mutation in exon 3 at position 564 of C>A that results in the substitution of leucine for phenylalanine.

III. Mutation of Mesp2 Yields Multiple Forms of SCD

Mesp2 encodes bHLH-type transcription factor, MesP2. The expression of the gene is observed in the nascent mesoderm, and subsequently in the rostral presomitic mesoderm. It is only expressed for a brief period during embryogenesis, in a highly restricted domain in the presomitic mesoderm.

The Mesp2 gene is predicted to produce a transcript of 1,191 bp encoding a protein of 397 amino acids with a predicted molecular weight of 41,744 Da and isoelectric point (pI) of 7.06. The human MesP2 protein has about 58.1% identity with mouse MesP2, and about 47.4% identity with human MesP1. Human MesP2 amino terminus contains a basic helix-loop-helix (bHLH) region encompassing St amino acids divided into an 11-residue basic domain, a 13-residue helix I domain, an 11-residue loop domain, and a 16-residue helix II domain. The loop region is slightly longer than that found in homologs such as paraxis. The length of the loop region is conserved between mouse and human MesP1, MesP2, and Thylacine 1 and 2, as well as chick mesogenin. In addition, both MesP1 and MesP2 contain a unique CPXCP motif immediately carboxy-terminal to the bHLH domain (see FIG. 2). The amino- and carboxy-terminal domains are separated in human MesP2 by a GQ repeat region also found in human MesP1 (2 repeats) but expanded in human MesP2 (13 repeats).

Recently, Whittock et al., *Am J Hum Genet.* 74: 1249-1254 (2004) studied a consanguineous family of Lebanese Arab origin with two offspring affected with a form of SCD milder than Jarcho-Levin syndrome. Affected individuals presented with truncal shortening and short necks but no other abnormalities. On radiological examination, thoracic vertebrae bore resemblance to those seen in SCD due to mutated DLL3, but the lumbar vertebrae appeared more angular and irregular. Genetic analysis showed that Mesp2 (Mesp2 [MIM 605195]) was mutated in those individuals having SCD by having a 4-bp (ACCG) duplication mutation in exon 1, termed "500-503 dup" [Genbank reference number MIM 605195.0001]. The parents were found to be heterozygous for the mutation, and an unaffected sibling was homozygous normal. Thus, the duplication segregates with disease in this family.

Herein, is described a different, unknown mutation, as illustrated in FIG. 1 and described in Examples 1 and 2, that appears to give rise to Jarcho-Levin syndrome and is demonstrably linked to SCD. This mutation, termed "E103stop" was discovered during investigation of genes associated with the segmentation clock and SCD, and the pertinent results of that investigation is described herein.

The E103stop mutation results in the creation of a unique SpeI restriction enzyme site in Mesp2. Those of ordinary skill in the art will appreciate that a variety of restriction enzyme sites can be used in conjunction with SpeI to screen for the presence or absence of the E103stop mutation. An illustrative use of SpeI to detect the presence and absence of the E103stop mutation is provided herein in Example 2. Further, because it appears that mice heterozygous for a mutation to Mesp2 are normal and fertile (Saga et al. 1997) as are humans who are heterozygous for the 500-503 dup mutation (Whittock et al. 2004), it is likely that humans heterozygous for E103stop are also phenotypically normal. Consequently, normal appearing individuals will be unaware that they carry a potential congenital defect. Screening (or testing) may be used to assist in the genetic counseling of normal appearing individuals, either suspected to be carriers or desiring to ascertain whether they are, for the E103stop mutation and/or other genetic anomalies.

IV. Kits and Screening for Mesp2

It is envisioned that a variety of kits and screening methodologies may be used to ascertain the presence or absence of a mutation to Mesp2. The kit and screening methodology chosen will depend upon the user's circumstances and preferences. For example, a kit and screening methodology may be used to determine whether an individual is a carrier (heterozygous for the E103stop mutation), or is afflicted with, spondylocostal dysostosis (homozygous for the E103stop mutation). Screening may optionally include examination for other mutations associated with one or more forms of SCD (e.g. known mutations to DLL3, Mesp2, Jag1, or Lfng).

The kit comprises a container, instructions for analysis of the Mesp2 mutation E103stop and optionally other mutations indicative of SCD, and a means for detecting the presence or absence of at least a Mesp2 nucleic acid sequence in a biological sample from a subject. The kit may include PCR primers that will amplify a portion of the Mesp2 gene regardless of whether the E103stop mutation is present; or alternatively, the PCR primers will only amplify a portion of the Mesp2 gene if the mutation is (or alternatively is not) present. Examplary primers are provided herein in Example 1. One of skill in the art will recognize that primers may be based on any portion of Mesp2 as long as the resulting product is suitable for the detection of the E103stop mutation.

In kits designed to amplify a portion of the Mesp2 gene regardless of whether the E103stop mutation is present, it is expected to be beneficial for the PCR primers to flank the E103stop mutation site such that the mutation site is amplified. The amplified product may then be directly sequenced using any of the standard methods available to one of ordinary skill in the art. The kit may include reagents and instructions for such sequencing. Oligotyping my also be used, and may be particularly appropriate where polymorphic sequences may occur. For example, oligotyping may be particularly applicable for batch or linkage analyses of mulitple samples to ascertain the presence or absence of polymorphisms within a family or population. See Mabilat and Courvalin. *Antimicrobial Agents & Chemotherapy* 34(10): 2210-2216 (1990).

Alternatively, the kit may include a combination of restriction digest enzymes, including Spe I, that may be used to disgest the PCR product(s) generated. In such kits, it is expected that digest products of specified size(s) will be indicative of either the presence or absence of the E103stop mutation and any other mutation being analyzed. Visualization and determination of the size(s) of the digest product(s) may be accomplished with either standard or pulsed-field agarose gel electrophoresis. Those of skill in the art will recognize that a variety of other current methods may be used to determine the size of the digest products.

Those of skill in the art will also recognize that a number of techniques including PCR-RFLP, ligase chain reaction (LCR), oligotyping using sequence specific primers, oligotyping using sequence specific oligonucleotide probes, single-stranded conformation polymorphism, single base pair primer extension (or single nucleotide polymorphism (SNP) primer extension), and direct sequencing may be incorporated into a screening method to analyze results produced by using the kit.

Exemplary kits for use in single base pair primer extension will include a primer designed to anneal to the sequence adjacent to the SNP site (e.g. position 307 of exon 1 of Mesp2). Once the primer anneals, single-base extension occurs by the addition of the complementary labeled ddNTP (e.g. a dye terminator) to the annealed primer. For example, each of the four ddNTPs may be fluorescently labeled with a different color dye. (The skilled artisan will recognize that other labels may be used.) The result is marker fragments for different SNP alleles that are all the same length, but vary by color. Labelled alleles may be detected by electrophoresis and fluorescence detection, where the allele of a single marker appears as different colored peak at roughly the same size in the electropherogram plot. It is expected that the size of the different allele peaks will vary slightly due to differences in molecular weight of the dyes. Data can then be analyzed using software designed to correlate size with genotype.

If desired, the single base pair primer extension assay can be modified such that a primer anneals and single-base extension occurs only in the presence, or alternatively in the absence, of a specific SNP. Here, a primer may anneal and be extended only in the presence, or alternatively the absence, of the E103stop mutation.

A number of variations of single base pair primer extension are known in the art, including those described in U.S. Pat. Nos. 7,074,597, 7,033,753, 6,573,047, 6,458,544, and 6,355,433 and incorporated herein by reference to the extent that they provide or teach exemplary methodologies or techniques, It is envisioned that single base pair primer extension assays may be easily conducted using a microarray to examine the SNP represented by the E103stop mutation.

In still other kits and screening methodologies, a nucleic acid probe, or oligonucleotide, comprising at least 50% homology to SEQ ID NO. 2, or its compliment, is provided in addtion to a container and instructions for screening and analysis. Such probe comprises at least about 50%, about 65%, about 75%, about 85%: about 95%, about 96%, about 97%, about 98%, or about 99% or greater homology to SEQ ID NO. 2, or its complimentary sequence.

Nucleic acid probes or primers may be labeled with a detectable marker such as an enzyme, biotin, radionuclide, fluorophore, luminophore, enzyme inhibitor, coenzyme, luciferin, paramagnetic metal or spin label. It is preferred that the nucleic acid probe or primer is capable of selectively detecting a single point mutation, in particular the E103stop mutation.

The nucleic acid probe or primer is contacted with a biological sample comprising genomic DNA anticipated to contain Mesp2 genetic code and hybridized or bound to the sample. Analysis of the hybridized, or bound, product is conducted according to standard protocols to determine the presence or absence of mutated Mesp2 genetic material. Such standard protocols, which involve the molecular manipulation of nucleic acids, are known to those skilled in the art. See generally Ausubel et al, "Short Protocols in Molecular Biology," John Wiley and Sons (1995) and Sambrook et al., "Molecular Cloning, A Laboratory Manual," second ed., Cold Spring Harbor Laboratory Press (1989).

Kits may also include similar types of probes or PCR primers for other heritable diseases or the genes associated with them. For example, kits may include a means of detecting mutation in DLL3, Lfng, Jag1, and/or detection of the 500-503 dup mutation to Mesp2. In such kits, the means chosen to detect such mutations will be similar to those means described herein for detecting the E103stop mutation in Mesp2.

Those of skill in the art will recognize that the size of the DNA fragment(s) produced will be determined by both the presence or absence of the E103stop mutation (and any other mutations to be screened) and the choice of LCR probes, PCR primers, or nucleic acid probes used. Thus, if desired, DNA fragments of different sizes could be diagnostic for the presence or absence of the E103stop mutation, as well as the presence of absence of other genetic mutations being screened. For example, the selection of different primers could yield fragments lengths of about 10, 15, 20, 25, 50, 75, 100, 150, 200, 300, 500, 750, 1000, 1250, 1500, 1750, 2000 or larger. Alternatively, the primers could be selected such that a DNA fragment, or particular fragment size, is only generated in either the presence or absence of the mutation. Those of skill in the art will recognize that the generation of a PCR product of a specified size could be indicative of either the presence or absence of a Mesp2 mutation or mutation associated with DLL3 Lfng, Jag1, or other gene, linked to SCD.

Those of skill in the art will also recognize that different sized DNA fragments may result from using a combination of compatible restriction enzymes to achieve DNA fragments of diverse, yet easily identified, sizes where the presence of a specific size fragment is unique and indicates the presence of the E103stop mutation or other mutation linked to SCD. A skilled artisan will be able to selectively choose the fragment sizes that are indicative of the E103stop, or other, mutation. It is likely that the choice will be influenced by the artisan's immediate objectives. For example, suitable choices for a simple screening may differ from those chosen for a complex linkage analysis.

After screening individuals for the presence of absence of the DNA fragment indicative of the mutation, samples from those individuals showing positive results may be further characterized, for example by direct sequence analysis, to confirm that the mutation is present.

Provided herein is a means for the rapid screening of individuals to determine whether they carry a Mesp2 gene having the E103stop mutation and optionally other mutations associated with SCD. It will be appreciated by those of skill in the art that the methods described herein may be combined with similar types of screening methods to determine the presence or absence of multiple mutations to multiple genes at the same time.

It is expected that this type of genetic screening will be particularly useful for the early diagnosis of SCD in newborns, infants, and adolescents so that these individuals may obtain early treatment. It is also expected that this type of genetic screening will be useful in counseling couples and individuals considering parenthood. For example, different forms of SCD are clearly linked to a variety of genetic mutations. In some instances, these forms of SCD are phenotypically similar but caused by different genetic mutations, and some forms are less severe than others.

DEFINITIONS

Unless defined otherwise, all technical and scientific terms used herein have the same meaning as is commonly understood by one of skill in the art to which this invention belongs. All patents and publications referred to herein are incorporated by reference herein.

"Subject" as used herein means a living organism having a central nervous system. Suitable subjects include: mammals, humans, mice, rats, dogs, cats, cattle, swine, sheep, and ungulates.

"Biological sample" as used herein means any tissue, organ, or bodily fluid from which genomic DNA can be isolated.

Numerous "bodily fluids" may be used as a suitable source of the biological sample, as they contain genomic DNA. The skilled artisan will appreciate that the choice of bodily fluid will depend upon both the health and maturity of the subject being examined and any other purposes of the examination. Bodily fluids are found in the bodies of men, women, children, and/or fetuses. Some may be found in animals as well. They include fluids that are excreted or secreted from the body as well as fluids that normally are not. These respective fluids include: amniotic fluid surrounding a fetus (which is released to the outside world in childbirth); aqueous humour; bile; blood and blood plasma; cerumen also known as earwax; Cowper's fluid or pre-ejaculatory fluid; chyle; chyme; female ejaculate; interstitial fluid; lymph; menses; breast milk; mucus (including snot and phlegm); pleural fluid; pus; saliva; sebum (skin oil); semen; serum; sweat; tears; urine; vaginal lubrication; and vomit. Internal bodily fluids, which are not usually leaked or excreted to the outside world, include: cerebrospinal fluid surrounding the brain and the spinal cord; synovial fluid surrounding bone joints; intracellular fluid is the fluid inside cells; blood; aqueous humour and vitreous humour; and the fluids in the eyeball.

"Epithelial cells", or epitheliun, line both the outside (skin) and the inside cavities and lumen of animal and human bodies. The outermost layer of skin is composed of dead stratified squamous epithelial cells, as are the mucous membranes lining the inside of mouths and body cavities. Other epithelial cells line the insides of the lungs, the gastrointestinal tract, the reproductive and urinary tracts, and comprise the exocrine and endocrine glands. The skilled artisan will appreciate that any of these organs and tissues may be a source of epithelial cells and can be used as the source of the biological sample in practicing the invention.

"Jarcho-Levin syndrome" as used herein refers to a form of spondylocostal dysostosis or congenital scoliosis which results in block vertebrae and fused ribs. The specific vertebrae and ribs involved may vary from case to case, as may the severity of the deformities.

"Spondylocostal dysostoses (SCD)" is used broadly herein to refer to a heterogenous group of disorders with severe axial skeletal malformations that includes Jarcho-Levin syndrome, spondylo-thoracic dysostosis (STD), both autosomal recessive and autosomal dominant disorders, costovertebral dysplasia, and abnormal vertebral segmentation (AVS).

For purposes of the present invention, "complementarity", "complementary" and variants thereof refer to the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand, Similarly, wherever guanine is found in one strand, cytosine is found in the other. The greater the relatedness between the nucleotide sequences of two DNA segments, the greater the ability to form hybrid duplexes between the strands of the two DNA segments. Herein, unless otherwise indicated, a "complementary sequence" of a specifically identified nucleotide sequence (i.e. by SEQ ID NO.) means a sequence having 100% complementarity to the specified sequence.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle. PCR is used to amplify DNA millions of fold, by repeated replication of a template, in a short period of time. (Mullis et al, Cold Spring Harbor Symp. Quant. Biol. 51:263 273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

"Ligase chain reaction" (LCR) is another method of DNA amplification similar to PCR and useful for detecting single base mutations. LCR differs from PCR because it amplifies the probe molecule rather than producing amplicon through polymerization of nucleotides. Basically, a primer is synthesized in two fragments and annealed to the template with the possible mutation at the boundary of the two primer fragments. Ligase will ligate the two fragments if they match exactly to the template sequence. LCR uses both a DNA polymerase enzyme and a DNA ligase enzyme to drive the reaction. Subsequent PCR reactions will amplify only if the primer is ligated.

"Encoded by" refers to a nucleic acid sequence which codes for a polypeptide sequence, wherein the polypeptide sequence, or a portion thereof, contains an amino acid sequence of at least 3 amino acids, more preferably at least 8 amino acids, and even more preferably at least 15 amino acids from a polypeptide encoded by the nucleic acid sequence.

"Identity," "identical," and derivations thereof refer to the relatedness of two sequences on a nucleotide-by-nucleotide basis or amino acid-by-amino acid basis over a particular comparison window or segment. Thus, identity is defined as the degree of sameness, correspondence or equivalence between the same strands (either sense or antisense) of two DNA segments or the primary structure of two polypeptides.

A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, a "nucleic acid fragment or sequence" is a polymer of DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. A "fragment" of a specified polynucleotide or nucleic acid sequence refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.

The terms "homology", "homologous " "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The phrase "single base pair primer extension" refers to a template-dependent extension reaction comprising extending a primer in the presence of the target nucleic acid sequence and a mixture of nucleotides (dATP, dTTP, dCTP, and dGTP). At least one type of nucleotide is labeled and extendible. One or more non-extendible nucleotides may also be present in the reaction and contain a different label than the extendable nucleotide. The labeled extendible nucleotide, and where present the labeled non-extendible nucleotide, is complementary to a specific allelic form of the target nucleic acid sequence. For example, the extendible nucleotide may be complementary to the wild-type Mesp2 sequence and the non-extendable nucleotide may be complementary to the recessive form of Mesp2 that is linked to Jarcho-Levin syndrome. Detection of incorporation of labeled nucleotide into the extended primer and its identification indicates that the identity of the nucleotide at the allelic site. The incorporated, labeled nucleotide may be detected by a variety of known means, including identification of the label and/or the size of the extended primer by methods such as gel electrophoresis and high performance liquid chromatography, "Single nucleotide polymorphisms" or SNPs are single base-pair differences between two copies of a deoxyribonucleic acid sequence that occur when a single nucleotide (A,T,C, or G) in the genome sequence is altered, A convenient method for detecting SNPs is restriction fragment length polymorphism (SNP-RFLP). See Sokolov. *Nucleic Acids Res.* 18(12): 3671 (1990); Patil, et a., *Current Protocols in Human Genetics*, vol. 1, unit 2.9.1-2.9.16 (2000). If one allele contains a recognition site for a restriction enzyme while the other does not, digestion of the two alleles will give rise to fragments of different length. Currently, existing SNPs are most easily studied using microarrays.

A "primer" is a single-stranded oligonucleotide capable of acting as a point of initiation of template-directed DNA synthesis under appropriate conditions (i.e., in the presence of four different nucleoside triphosphates and usually in the presence of an agent for polymerization, such as, DNA or RNA polymerase or reverse transcriptase unless otherwise stated) in an appropriate buffer and at a suitable temperature. The appropriate length of a primer depends on the intended use of the primer but typically ranges from 8 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer site" refers to the segment of the target DNA to which a primer hybridizes. The term "primer pair" means a set of primers including a 5' "upstream primer" that hybridizes with the 5' end of the DNA sequence to be amplified and a 3' "downstream primer" that hybridizes with the complement of the 3' end of the sequence to be amplified.

An extended primer may be separated from the remaining reaction by a variety of known means. For example, a primer may include an attachment moiety that is a first member of a binding pair and when contacted with a second member of a binding pair that is immobilized on a substrate, such as a microarray, the primer becomes immobilized to the substrate due to the interaction between the two members of the binding pair. In another example, an extended primer may be separated by denaturing it from the target nucleic acid sequence. Such variations as these, alone or in conjunction with multiple labels, allows for determining whether a subject is homozygous normal (wild-type), heterozygous (carrier), or homozygous recessive (afflicted) for a particular SCD, such as Jarcho-Levin syndrome.

Herein, in reference to nucleic acid sequence position "adjacent to" means substantially near such that two sequences are in close proximity to each other but not overlapping. Sequences may be separated from each other by one or more nucleotides. When reference is made to a primer hybridizing "adjacent to" a nucleotide site, it is meant that the primer preferably hybridizes immediately 5' to the site, or optionally, that the primer hybridizes 5' to the site, so long as the nucleotide base that appears at the variant site of the template strand does not appear in the region between the 3' end of the primer and the variant site of the template strand.

Herein, "ddNTP" refers to the four general groups of dideoxynucleic acids. Specifically, ddATP, ddCTP, ddGTP, and ddTTP.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Sequencing of E103stop Mesp2 Mutation

I. Materials and Methods:

Genomic DNA was isolated and prepared from patient blood samples using a PAXgene Blood DNA kit according to the manufacturer's protocol (PreAnalytiX, a Qiagen/BD company, Valencia, Calif.). Mesp2 exon sequences were amplified from genomic DNA using the Polymerase Chain Reaction (PCR) according to the following protocols: Mesp2 exon 1 was amplified using the M1 1F primer (5'GACAC-CTCTCTGCAACCTG3' SEQ ID NO. 3) and the M1 1R primer (5'CCTGGAGTAGATAAGCTGGG3' SEQ ID NO. 4) described in Whittock et al., 2004. PCR was accomplished using 25 ng of genomic DNA, 0.6 units FailSafe™ enzyme (Epicentre Biotechnologies, Madison, Wis.), 0.32 µM primers, and FailSafe™ buffer D (Epicentre Biotechnologies). The reactions were then amplified using the following thermocycler protocol: 95° C. 5 min, 40×(95° C. 30s, 55° C. 30s, 72° C. 1.5 min), 72° C. 10 min. Mesp2 exon 2 was amplified using the M1 2F primer (5'CCAGCCATACCATGGCAAC3' SEQ ID NO. 5) and the M2 2R primer (5'CCAAGCTACAG-GACTGATTC3' SEQ ID NO. 6) described in Whittock et al., 2004. PCR was accomplished using 25 ng of genomic DNA, 0.5 units Biolase Taq polymerase (Bioline, USA Inc., Randolph, Mass.), 2.0 mM MgCl$_2$ and standard PCR buffer. The reactions were then amplified using the following thermocycler protocol: 95° C. 5 min, 40×(95° C. 30s, 60° C. 30s, 72° C. 1 min), 72° C. 10 min.

The PCR products were purified using Edge ExcelaPure 96-Well UF PCR Purification plates (Edge Biosystems, Gaithersburg, Md.) and sequenced using BigDye® v3.1 chemistry on a 3730 DNA Analyzer (Applied Biosystems, Foster City, Calif.) with the primers described above plus 3 additional primers to cover exon 1 (AAGATCGAGACGCT-GCGCCT, SEQ ID NO. 7, CACTGCAGACTCTCCTCGCT, SEQ ID NO. 8, and CAAGGGCAGGGGCAAGGACAG, SEQ ID NO. 9). Sequences of patient samples were compared to Mesp2 references sequences in Genbank using SeqScape® v2.5 software (Applied Biosystems).

Figure 2:
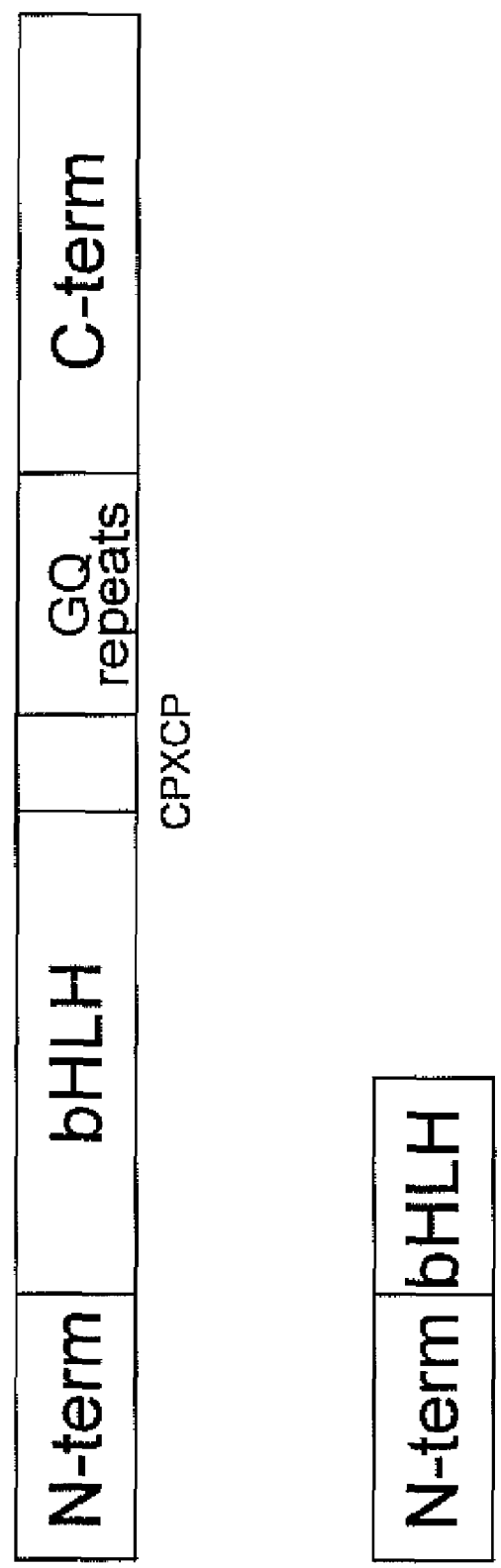
FIG. 2. Comparison of Mesp2 full length protein vs. truncated protein caused by the E103stop mutation. The full length Mesp2 protein (top) has an N-terminal domain followed by a basic helix-loop-helix domain (bHLH), a region rich in glycine and glutamine residues (GQ repeats) and a C-terminal region. Between the bHLH domain and the GQ repeats is a conserved CPXCP motif. The predicted protein resulting from the E103stop mutation (bottom) has a short non-functional bHLH domain and is missing the other domains.
Figure 3:
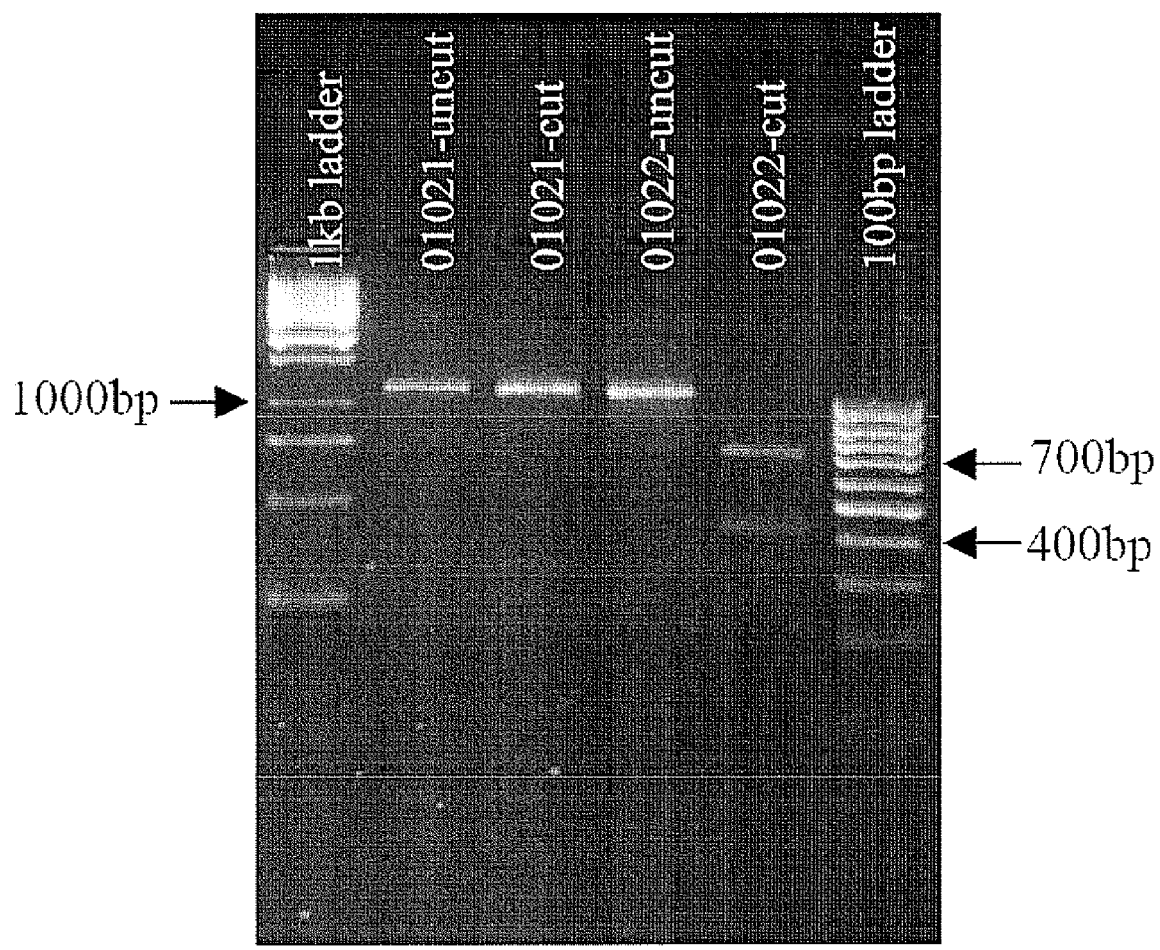
FIG. 3. Detection of E103stop mutation by restriction digest with Spe I. The 307G>T mutation creates a new Spe I restriction enzyme site in Mesp2. Lane 1: DNA size ladder; Lane 2: uncut DNA from a patient not having the E103stop mutation (01021); Lane 3: DNA from the same patient (01021) cut with Spe I; Lane 4 uncut DNA from a patient having the E103stop mutation (01022); Lane 5: DNA from the same patient (01022) cut with Spe I. Lane 6: DNA size ladder.

II. Results:

A single nucleic acid base pair substitution (307G>T) in Mesp2 was found in a human subject with Jarcho-Levin syndrome of Puerto-Rican decent (see FIG. 1 and FIG. 3, sample 01022). The substitution results in the replacement of a glutamic acid codon (GAG) at amino acid position 103 of exon 1 of the Mesp2 gene with a stop codon (TAG) (FIG. 1, boxed nucleotides). The E103stop mutation occurs in the middle of the basic helix loop helix domain and is predicted to encode a non-functional protein (FIG. 2). The subject is homozygous for the mutation, suggesting that no functional MesP2 protein is produced by the subject.

The E103stop mutation was subsequently found in additional Puerto Rican patients, indicating that the mutation is commonly found in individuals with Jarcho-Levin syndrome of Puerto Rican decent. Seven patients were sequenced and are homozygous for the mutation, and six obligate carriers were found to be heterozygous for the mutation (see Table 1).

TABLE 1

Summary of Puerto Rican patients with E103stop mutation.

| Sample ID | Affected status | E103stop mutation | homozygous, heterozygous |
| --- | --- | --- | --- |
| 010529-01(B) | AF | yes | homoz |
| 021221-03 | AF | yes | homoz |
| 060406-01 | OC | yes | het |
| 060406-03 | AF | yes | homoz |
| 060406-05 | OC | yes | het |
| 060406-07 | AF | yes | homoz |
| 060406-08 | OC | yes | het |
| 990706-01 | AF | yes | homoz |
| 980615-01 | OC | yes | het |
| 980615-03 | OC | yes | het |
| 980615-04 | AF | yes | homoz |
| 980524-01 | AF | yes | homoz |
| 980524-03(A) | OC | yes | het |

[1]The table lists the patient IDs, affected status (AF = affected, OC = obligate carrier), presence of the E103stop mutation and whether the patient is homozygous (homoz) or heterozygous (het) for the mutation. The patients are described in Cornier et al. Am J Med Genet 128A: 120-126 (2004).

These results demonstrate a clear linkage between the E103stop mutation and Jarcho-Levin syndrome in individuals of Puerto Rican descent and the utility of the mutation to detect carriers of the syndrome, as well as, those afflicted with SCD.

Example 2

Rapid Screening for the Presence of E103stop Mesp2 Mutation

In addition to amplifying and sequencing the pertinent section of exon 1 of Mesp2 genomic DNA, subjects may be rapidly screened for the presence or absence of the E103stop mutation by the use of restriction enzymes. Specifically, the 307G>T mutation creates a new Spe I restriction enzyme site (A/CTAGT) which can be used in a diagnostic test to screen for the likelihood of spondylocostal dysostosis/Jarcho-Levin syndrome. This Spe I restriction site is absent in wild-type (Wt) Mesp2. If the E103stop (307G>T) is present, digestion by SpeI yields two DNA fragments that are respectively 706 bp and 411 bp in size. If the E103stop mutation is absent, a 1117 bp fragment is seen.

I. Material and Methods:

Genomic DNA was isolated from biological samples obtained from individuals either having Wt Mesp2 (FIG. 3, sample 01021) or mutant Mesp2 (FIG. 3, sample 01022). The genomic DNAs were isolated using standard isolation techniques such as those described in *Current Protocols in Molecular Biology*, (1998) Unit 2.2, pub. John Wiley & Sons, Inc., incorporated herein by reference.

Polymerase chain reaction (PCR) was done by amplifying exon 1 of Mesp2 from the isolated genomic DNAs with the M1 1F and M1 1R primers (see Example 1) using conditions similar to those described in Example 1. The PCR products were digested with Spe I under conditions suitable for Spe I digestion.

The digested PCR products were then separated from one another using agarose gel electrophoresis. Protocols for standard and pulsed-field agarose gel electrophoresis can be found in *Current Protocols in Molecular Biology*, (2000) Units 2.5A and 2.5B, pub. John Wiley & Sons, Inc. and are incorporated herein by reference.

II. Results and Conclusions:

As shown in FIG. 3, lane 3, Spe I did not digest the amplified segment of Wt Mesp2 and the amplified product is approximately 1117 bp in length. In contrast, Spe I did digest the amplified product of mutant Mesp2, FIG. 3, lane 5, to produce two DNA fragments, 706 bp and 411 bp respectively. Thus, the method provides a means of determining the presence or absence of the E103stop mutation in humans.

Biological samples from the patients in Example 1 and eight other patients, also diagnosed with either having Jarcho-Levin syndrome or being a carrier of it, were also subjected to SpeI RFLP. All of the samples from the patients in Example 1 produced the expected DNA fragments of 706 and 411 bp. But, of the remaining eight samples only one half were positive for the E103stop mutation. (See Table 2.) These results suggest that either mutation in a second unidentified gene may also cause this syndrome or that these individuals are affected by one or more genetically different, but phenotypically similar, subclasses of the disease.

TABLE 2

Summary of detection of the E103stop mutation in other patients.

| Sample ID[1] | Affected status | E103stop mutation | homozygous, heterozygous, WT |
|---|---|---|---|
| 030729-03(A) | not listed | yes | het |
| 050211-03 | AF | yes | het |
| 000826-04(C) | AF | yes | het |
| 060406-04 | AF | no | WT |
| 060406-06 | AF | yes | het |
| 060406-09 | OC | no | WT |
| 060406-10 | AF | no | WT |
| 980524-04 | OC | no | WT |

[1]Notations as in Table 1.

Example 3

Kits to Rapidily Screen for Mutations

As exemplified above, a variety of screening methods may be used to detect the E103 stop mutation to Mesp2 and to determine the genetic mutation associated with a class or subclass of SCD, in particular with Jarcho-Levin syndrome. Kits encompassing compositions to practice one or more of these methods, either separately or in conjunction with one another, are provided by the invention. At a minimum, such kits will include instructions and appropriate components for determining the presence or absence of the E103stop mutation.

It is envisioned that a preferred kit may use single base pair primer extensions to detect single nucleotide polymorphisms, or SNPs, and include a microarray. A variety of microarrays are presently known in the art and suitable for SNP analysis. At a minimum, such kits will include a primer designed to anneal to the sequence adjacent to the E103stop mutation site, i.e. position 307 of exon 1 of Mesp2. The kit may provide further reagents for restriction fragment length polymorphism of the SNP (SNP-RFLP) and may be used in conjunction with software to size and genotype the data. See Sokolov. *Nucleic Acids Res.* 18(12): 3671 (1990); Patil, et al., *Current Protocols in Human Genetics*, vol. 1, unit 2.9.1-2.9.16 (2000).

A kit may include forward and reverse PCR primers to amplify the segment of Mesp2 containing the E103stop mutation. The PCR primers may be those described in Example 1 or others that are designed to anneal to different portions of Mesp2. Additionally, the primers may be selected such that they amplify a fragment of Mesp2 containing positions diagnostic for both the E103stop and the 500-503 dup mutations. The kit may include reagents for direct sequencing and/or restriction digest as exemplified in Examples 1 and 2. In the case of restriction digest it is envisioned that kits will include at a minimum SpeI enzyme and may also contain additional, compatible reagents. RFLP pattern analysis may then be used to determine if either or both mutations are present.

It is envisioned that any of these kits may also include instructions and regeants for determining the presence or absence of mutations to DLL3, Lunatic fringe, and other mutations to Mesp2 that are linked to one or more forms of SCD. (See Bulman et al (2000); Sparrow et al (2002); Bonafé et al. (2003); Turnpenny et al. (2003); Whittock et al. (2004a), (2004b); and Sparrow, et al (2006), each of which is incorporated by reference to the extent that they provide or teach such mutations.) In such instances, it is expected that the method used to detect such additional mutations will parallel the method used to detect the E103stop mutation.

Any of these kits may include reagents suitable for an alternative means of detecting the E103stop mutation, and possibly other mutations, associated with SCD. For example, reagents useful for ligase chain reaction (LCR), oligotyping using Sequence Specific Primers (SSP), oligotyping using Sequence Specific Oligonucleotide Probes (SSOP), and single-stranded conformation polymorphism (SSCP) may be optionally included in kits that are useful for single base pair primer extension, SNP-RFLP, direct sequencing, or PCR.

The choice of kit will be determined in part by the objective(s) to be achieved, For example, a kit providing a microarray for single base pair primer extension may be more suited to analyze multiple biological samples for multiple mutations; whereas, a kit providing reagents for LCR may be more suited to analyze a few biological samples for a single mutation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

REFERENCES

The following references, as well as those cited within this specification, are specifically incorporated by reference to the extent that they provide or teach exemplary methodology, techniques and/or compositions supplemental to those employed herein.

1. U.S. Pat. No. 7,074,597
2. U.S. Pat. No. 7,033,753
3. U.S. Pat. No. 6,573,047
4. U.S. Pat. No. 6,458,544
5. U.S. Pat. No. 6,355,433
6. Ausubel et al., *Short Protocols in Molecular Biology*, John Wiley and Sons (1995).
7. Sambrook et al, *Molecular Cloning. A Laboratory Manual*, 2nd ed., Cold Spring Harbor Laboratory Press (1989).
8. Whittock N V, et al. *Clin Genet* 66: 67-72 (2004a).
9. Whittock, et al. *Am J Hum Genet.* 74(6); 1249-54 (2004b).
10. Saga, et al. *Genes & Develop* 11: 1827-1839(1997).
11. Cornier, et al. *Am J Med Genet* 128A: 120-126 (2004).
12. Campbell, et al. *Am J Med Genet* 128A: 132 (2004).
13. Ausubel, et al. (Eds.) *Current Protocols in Molecular Biology*, vol. 1, units 2-3 (2005).
14. Turnpenny and Kusumi. In Epstein, et al. (eds.) *Inborn Errors Of Development*. Oxford Univ. Press, NY, pp 470-481.
15. Bulman, et al. *Nature Genetics* 24: 438-441 (2000).
16. Sparrow, et at. *Am J Hum Genet.* 78(1): 28-37 (2006).
17. Turnpenny, et al. *J Med Genet* 40: 333-339 (2003).
18. Sparrow, ela *Int J Dev Biol* 46: 365-374(2002).
19. Bonafé et al. *Clin Genet* 64: 28-35 (2003).
20. Weinmaster and Kintner. *Annu Rev Cell Dev Biol* 19: 367-395 (2003).
21. Sokolov. *Nucleic Acids Res.* 18(12): 3671 (1990).
22. Patil, et al., *Current Protocols in Human Genetics*, vol. 1, unit 2.9.1-2.9.16 (2000).

What is claimed is:

1. A method of identifying a human subject having a mutation associated with Jarcho-Levin syndrome comprising:
   a) obtaining a biological sample from a human subject comprising genomic DNA of the human subject;
   b) detecting in the genomic DNA substitution of a thymine for a guanine at nucleotide position 307 of exon 1 of Mesp2, whereby detection of the substitution is indicative of a mutation associated with Jarcho-Levin syndrome.

2. The method of claim 1, wherein the biological sample is selected from the group consisting essentially of bodily fluid, epithelial cells, and a combination thereof.

3. The method of claim 1, wherein detection is selected from the group consisting essentially of PCR-RFLP, ligase chain reaction (LCR), oligotyping using Sequence Specific Primers (SSP), oligotyping using Sequence Specific Oligonucleotide Probes (SSOP), single-stranded conformation polymorphism (SSCP), direct sequencing, restriction digest, single base pair primer extension, and a combination thereof.

4. The method of claim 3, wherein detection comprises single base pair primer extension.

5. The method of claim 1, further comprising detection of the presence or absence of a second mutation linked to spondylocostal dysostosis, wherein the second mutation is selected from the group consisting of 500-503 dup [MIM 605195.0001] in Mesp2, a mutation in DLL3, a mutation in Lfng, and a combination thereof.

6. A method of identifying a human subject having a thymine to guanine substitution at nucleotide position 307 of Exon 1 of Mesp2 comprising determining whether a nucleic acid obtained from a biological sample of the human subject has an E103 stop mutation.

7. The method according to claim 6 further comprising correlating the presence of an E103 stop mutation in a nucleic acid of the human subject with the human subject having Jarcho-Levin syndrome or being a carrier for Jarcho-Levin syndrome.

8. The method according to claim 6, wherein the biological sample is selected from the group consisting essentially of bodily fluid, epithelial cells, and a combination thereof.

9. The method according to claim 6, wherein the determining step is selected from the group consisting essentially of PCR-RFLP, ligase chain reaction (LCR), oligotyping using Sequence Specific Primers (SSP), oligotyping using Sequence Specific Oligonucleotide Probes (SSOP), single-stranded conformation polymorphism (SSCP), direct sequencing, restriction digest, single base pair primer extension, and a combination thereof.

10. The method according to claim 9, wherein determining step comprises single base pair primer extension.

11. The method according to claim 6, further comprising detecting of the presence or absence of a second mutation linked to spondylocostal dysostosis, wherein the second mutation is selected from the group consisting of 500-503 dup [MIM 605195.0001] in Mesp2, a mutation in DLL3, a mutation in Lfng, and a combination thereof.

* * * * *

```
                         SEQUENCE LISTING

<160> NUMBER OF SEQ ID NOS: 12

<210> SEQ ID NO 1
<211> LENGTH: 21
<212> TYPE: DNA
<213> ORGANISM: Homo sapiens

<400> SEQUENCE: 1
gccctgcacg agttgcgccg c                                                     21

<210> SEQ ID NO 2
<211> LENGTH: 21
<212> TYPE: DNA
<213> ORGANISM: Homo sapiens

<400> SEQUENCE: 2
gccctgcact agttgcgccg c                                                     21

<210> SEQ ID NO 3
<211> LENGTH: 19
<212> TYPE: DNA
<213> ORGANISM: Homo sapiens

<400> SEQUENCE: 3
gacacctctc tgcaacctg                                                        19

<210> SEQ ID NO 4
<211> LENGTH: 20
<212> TYPE: DNA
<213> ORGANISM: Homo sapiens

<400> SEQUENCE: 4
cctggagtag ataagctggg                                                       20

<210> SEQ ID NO 5
<211> LENGTH: 19
<212> TYPE: DNA
<213> ORGANISM: Homo sapiens

<400> SEQUENCE: 5
ccagccatac catggcaac                                                        19
```

```
<210> SEQ ID NO 6
<211> LENGTH: 20
<212> TYPE: DNA
<213> ORGANISM: Homo sapiens

<400> SEQUENCE: 6
ccaagctaca ggactgattc                                               20

<210> SEQ ID NO 7
<211> LENGTH: 20
<212> TYPE: DNA
<213> ORGANISM: Homo sapiens

<400> SEQUENCE: 7
aagatcgaga cgctgcgcct                                               20

<210> SEQ ID NO 8
<211> LENGTH: 20
<212> TYPE: DNA
<213> ORGANISM: Homo sapiens

<400> SEQUENCE: 8
cactgcagac tctcctcgct                                               20

<210> SEQ ID NO 9
<211> LENGTH: 21
<212> TYPE: DNA
<213> ORGANISM: Homo sapiens

<400> SEQUENCE: 9
caagggcagg ggcaaggaca g                                             21

<210> SEQ ID NO 10
<211> LENGTH: 8
<212> TYPE: PRT
<213> ORGANISM: Homo sapiens

<400> SEQUENCE: 10

Ala Leu His Glu Leu Arg Arg Phe
1               5

<210> SEQ ID NO 11
<211> LENGTH: 3
<212> TYPE: PRT
<213> ORGANISM: Homo sapiens

<400> SEQUENCE: 11

Ala Leu His
1

<210> SEQ ID NO 12
<211> LENGTH: 4
<212> TYPE: PRT
<213> ORGANISM: Homo sapiens

<400> SEQUENCE: 12

Leu Arg Arg Phe
1
```